United States Patent
Carrier et al.

[11] Patent Number: 5,352,315
[45] Date of Patent: Oct. 4, 1994

[54] BIOMEDICAL ELECTRODE

[75] Inventors: Levi A. Carrier; Jay M. Ruehlen, both of Longmeadow; Nilay Sankalia, Agawam, all of Mass.

[73] Assignee: Ludlow Corporation, Exeter, N.H.

[21] Appl. No.: 147,442

[22] Filed: Nov. 5, 1993

Related U.S. Application Data

[63] Continuation of Ser. No. 728,876, Jul. 12, 1991, abandoned.

[51] Int. Cl.$^5$ .................. B32B 31/12; B32B 31/18
[52] U.S. Cl. .................. 156/267; 156/269; 156/277; 156/289; 156/324; 128/640; 607/149; 607/152
[58] Field of Search .............. 156/277, 324, 267, 269, 156/289; 128/639, 640, 641, 798, 802; 607/149, 152

[56] References Cited

U.S. PATENT DOCUMENTS

| | | |
|---|---|---|
| 1,053,881 | 2/1913 | Scott et al. |
| 3,003,975 | 10/1961 | Louis |
| 3,083,169 | 3/1963 | Ueda |
| 3,547,105 | 12/1970 | Ramme et al. |
| 3,911,906 | 10/1975 | Reinhold, Jr. |
| 3,976,055 | 8/1976 | Monter et al. |
| 4,102,331 | 7/1978 | Grayzel et al. ............ 128/640 |
| 4,370,984 | 2/1983 | Cartmell |
| 4,391,278 | 7/1983 | Calahan et al. |
| 4,432,368 | 2/1984 | Russek ............ 128/802 X |
| 4,524,087 | 6/1985 | Engel |
| 4,551,925 | 11/1985 | Ericsson ............ 34/39 X |
| 4,554,924 | 11/1985 | Engel ............ 128/640 |
| 4,588,762 | 5/1986 | Mruk et al. ............ 156/327 X |
| 4,590,327 | 5/1986 | Nath et al. ............ 427/74 X |
| 4,657,023 | 4/1987 | Kuhn |
| 4,674,511 | 6/1987 | Cartmell |
| 4,674,512 | 6/1987 | Rolf |
| 4,679,563 | 7/1987 | Wada et al. |
| 4,694,835 | 9/1987 | Strand |
| 4,699,679 | 10/1987 | Cartmell et al. ............ 128/640 X |
| 4,736,752 | 4/1988 | Munck et al. ............ 128/802 X |
| 4,838,273 | 6/1989 | Cartmell ............ 128/640 |
| 4,842,768 | 6/1989 | Nakao et al. |
| 4,848,353 | 7/1989 | Engel |
| 4,852,571 | 8/1989 | Gadsby et al. ............ 128/640 |
| 4,890,622 | 1/1990 | Ferrari ............ 128/640 |
| 5,038,796 | 8/1991 | Axelgaard et al. ............ 128/802 X |
| 5,255,677 | 10/1993 | Schaefer et al. ............ 607/152 X |

FOREIGN PATENT DOCUMENTS

PCT/GB90/-01565  5/1991  PCT Int'l Appl.

Primary Examiner—Mark Osele
Attorney, Agent, or Firm—Richard H. Kosakowski

[57] ABSTRACT

A novel biomedical electrode comprising 1) a non-conductive backing layer with instructions printed on one surface, 2) an ink layer having either a) an ink comprising silver and silver salt, or b) a blend of inks including a first ink comprising silver and silver salt and a second ink comprising an inert carbon based material printed in a pattern onto the second surface of the non-conductive backing layer, 3) a conductive-adhesive electrolyte layer coated directly onto the inked surface of the non-conductive backing layer, and 4) a protective release liner which covers the conductive adhesive layer. Certain preferred embodiments correspond to situation wherein the body parts being monitored display diverse impedances. In those embodiments, parameters such as ink blend, ink amount (i.e., ink thickness and ink pattern) are varied in order to vary the impedance of a given electrode. These impedance distinct electrodes allow for the construction of a set of electrodes in which the varying impedances of the different electrodes compensate for the varying impedances of the different body parts. The construction of the electrode set also allows for a single line manufacturing process.

20 Claims, 10 Drawing Sheets

BIOMEDICAL ELECTRODE

This application is a continuation of applicaton Ser. No. 07/728,876, filed Jul. 12, 1991, now abandoned.

FIELD OF THE INVENTION

This invention relates to an electrode or a set of electrodes useful in detecting the electrical currents generated by biomedical events; to such electrode or electrodes with a homogeneously blended conductive ink layer thereof; to such electrode or electrodes with a solventless conductive adhesive layer thereof; and to a unique method of manufacturing such electrodes which insures economical production and predictable electrical characteristics.

BACKGROUND OF THE INVENTION

Prior disposable biomedical electrodes ("snap connector electrodes") were generally in the form of a pressure sensitive adhesive pad, with a snap connector extending through the surface of the pad so that a snap stud presented itself on the upper surface, while a metal plated conductive member presented itself on the under surface. The conductive metallic layer of this sensing element comprised silver, tin, or the salts of silver or tin. A sponge, saturated with electrolyte, was placed over the conductive member on the under surface, while leaving a border of pressure sensitive adhesive to make contact with the skin. The entire assembly was then covered with a protective carrier, or liner, which would be discarded prior to use. U.S. Pat. Nos. 3,805,769, 3,834,373, 3,923,042, 3,976,055, and 3,993,049 illustrate electrodes of this type. While possessing advantages over reusable needle or suction type electrodes, these early disposable electrodes were not only relatively expensive, but also tended to dry out during storage, thus limiting their useful shelf life.

More economical types of electrodes utilizing less expensive integral-connecting tabs ("tab type electrodes") have been disclosed in several patents, including U.S. Pat. Nos. 4,125,110, 4,365,634, 4,524,087, 4,543,958, and 4,674,512. However, construction of these products, especially those which use tin as a conductive layer, is such that they do not always comply with all of the standards established by governmental regulatory agencies and medical industry groups for such electrodes. In particular, the Association for the Advancement of Medical Instrumentation (AAMI) has set forth standards for various electrical characteristics of disposable biomedical electrodes. The specification for defibrillation recovery characteristics, which describes certain time-related, electrical dissipation properties of the electrode following repeated electrical shocks of defibrillation currents, is especially difficult for many of the above "tab-type" electrodes to meet. Thus, use of the tab type electrode would invite the possibility of an inordinate, life-threatening delay in obtaining electrocardiographic data following defibrillation. This, of course, severely limits the usefulness of such electrodes in a critical care environment. Accordingly, many of these products bear a caution label that they are not to be used where defibrillation is a possibility.

U.S. Pat. No. 4,852,571 addresses some of the shortcomings of these non-snap, tab-type electrodes, and discloses a disposable electrode which passes the electrical requirements as specified by AAMI. However, the '571 design requires two separate layers of conductive inks, comprising a "discontinuous layer" of silver/silver chloride ink over a layer of carbon ink, which must be applied in two separate steps. This dual step ink application requirement increases cost and decreases process control.

Electrodes using solventless gels which are both conductive and adhesive are disclosed in several patents including U.S. Pat. Nos. 4,524,087, 4,391,278, and 4,125,110. Such gels, also known in the art as "hydrogels", utilize either a thermal or an ultraviolet photo curing process in order to convert the conductive-adhesive hydrogel into its final form. However, in most cases, the cured hydrogel must first be laminated to the other electrode materials and then die cut into the desired electrode form. The lamination and die cut requirements present significant economical disadvantages. To avoid these disadvantages, "hot melt" type of adhesives have been introduced. While hot melt adhesives may be applied directly to the conductive ink in a hot melt process (thus avoiding lamination), their utility has thus far been limited since most hot melt adhesives require application temperatures in excess of 250° F., thereby excluding water based hot melts from consideration.

In addition to problems arising from the designs of the single prior art electrode, problems have also arisen in the deployment of electrode sets. In procedures such as ECG/EKG monitoring or stress testing, electrodes are placed at different sites on the human body. However, since the human body exhibits different skin impedance values at various sites, the electrode-to-skin impedance values at such sites can vary widely. If uncompensated, these variances may provide an inconsistent baseline to the monitoring equipment and generate inaccurate readings.

Lastly, experience has shown that different brand or models of monitors do not necessarily produce consistent results from the same electrode. Similar to the skin impedance problem discussed above, this phenomenon may also produce inaccurate readings.

In sum, the prior art possesses the following shortcomings:
a) snap connectors which were expensive;
b) tab type electrodes which had long defibrillation recovery times;
c) electrolyte adhesives which dried out;
d) hydrogel adhesives which required lamination prior to die cutting;
e) hot melt adhesives which could not be water base;
f) electrodes which did not compensate for impedance variances; and
g) bilayered inks which required dual step ink application.

Furthermore, because all of the above described electrodes required multiple manufacturing steps, the problems associated with process control are significant.

Thus, there exists a need for a safe, economical electrode or set of electrodes which can compensate for impedance variances and can be economically manufactured, preferably in a continuous process.

SUMMARY OF THE INVENTION

The present invention addresses many of the above-described disadvantages by providing a low cost, disposable biomedical electrode or set of electrodes which may be manufactured in a single pass through an assembly line, wherein 1) the impedances of distinctly identifiable electrodes may vary within a set thus compensating for the diverse impedances at different body sites or the specific requirements for certain monitoring equipment, 2) the conductive ink layer may be an inexpensive homogeneous blend of inks which can be coated directly to a non-conductive backing material without the need for a lamination step, 3) the conductive adhesive layer can be coated without lamination to the non-conductive backing layer/conductive ink layer and at a temperature suitable for water based adhesives, and 4) the set can be produced in a single pass through an assembly line.

More specifically, in one preferred embodiment, the biomedical electrode of the present invention comprises 1) a non-conductive backing layer with instructions printed on one surface, 2) a conductive ink layer having either a) an ink comprising silver and silver chloride or b) a homogeneous blend of inks including a first ink comprising silver and silver chloride and a second ink comprising an inert, carbon based material, wherein the conductive ink layer comprises a pattern printed onto the second surface of the non-conductive backing layer, 3) a conductive-adhesive electrolyte layer coated directly onto the patterned surface of the non-conductive backing layer, and 4) a protective release liner which covers the conductive adhesive layer. Certain preferred embodiments comprise a set of electrodes wherein the impedances of the electrodes within the set are varied in accordance with the impedance of the body sites being monitored. In those embodiments, parameters such as ink blend and ink amount (i.e., ink thickness and ink pattern) are varied in order to vary the impedance of a given electrode. These impedance distinct electrodes allow for the construction of a set of electrodes in which the varying impedances of the different electrodes compensate for the varying impedances which are observed at different body sites. The construction of the electrode set also allows for a single line manufacturing process. In other embodiments of the present invention, the impedance of each electrode within the set of electrodes may be the same.

DETAILED DESCRIPTION

A preferred biomedical electrode or set of electrodes of the present invention comprises 1) a non-conductive backing material which may contain artwork and/or instructions printed on a first surface, in register on each electrode, 2) a conductive ink layer comprising either a) an ink comprising a galvanic metal and a conductive salt or b) a homogeneous blend of inks including a first ink comprising a galvanic metal and a conductive salt and a second ink comprising an inert, carbon based material, which is printed directly onto a second surface of the non-conductive backing layer, in a pattern which is smaller in area than the non-conductive backing layer, and which is in register on each electrode, 3) a biocompatible conductive-adhesive electrolyte layer which is coated directly onto the patterned surface of the non-conductive backing material, leaving a dry edge for a connector, and 4) a protective release liner which covers the conductive adhesive layer.

Figure 1:
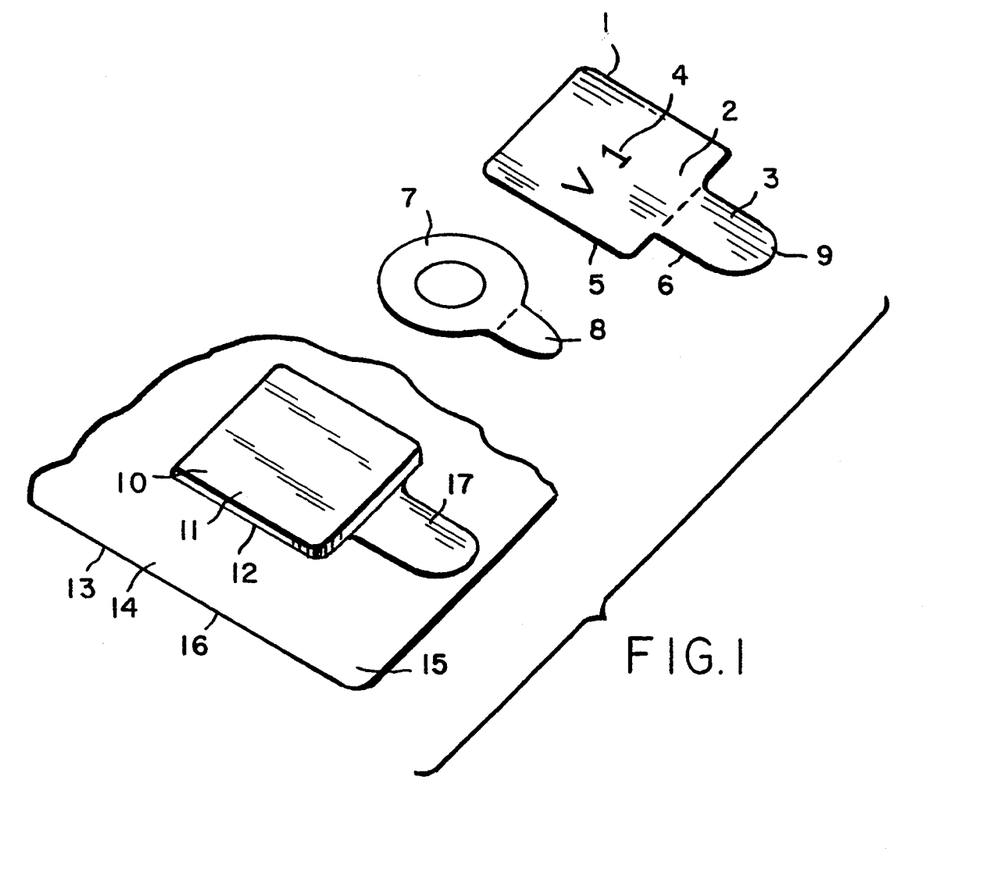
FIG. 1 is an exploded perspective view of a preferred biomedical electrode of this invention.
Figure 2A:
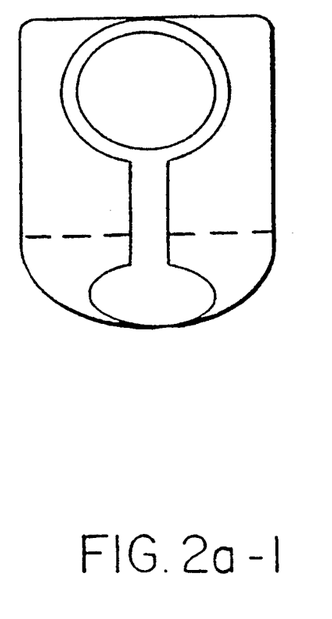
FIG. 2 is a top view illustrating various types of patterns of conductive ink which might be utilized in the biomedical electrodes of this invention.
Figure 2A:
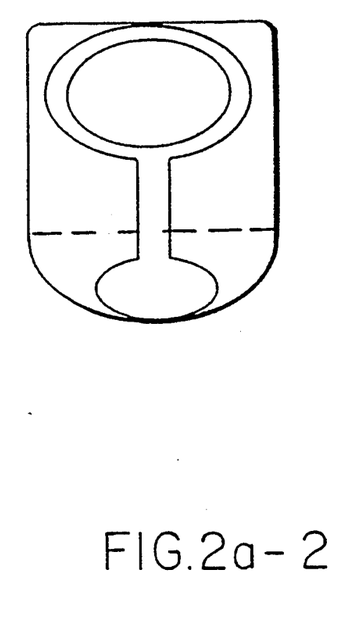
Figure 2A:
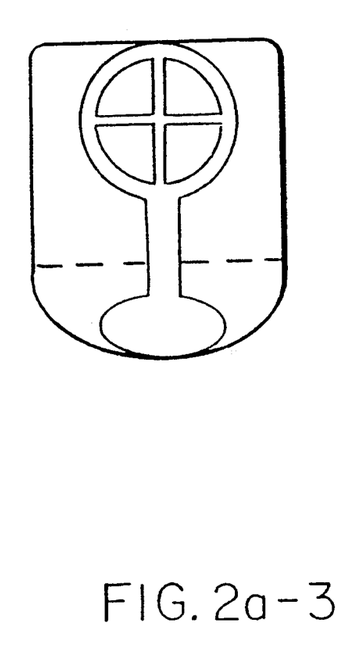
Figure 2A:
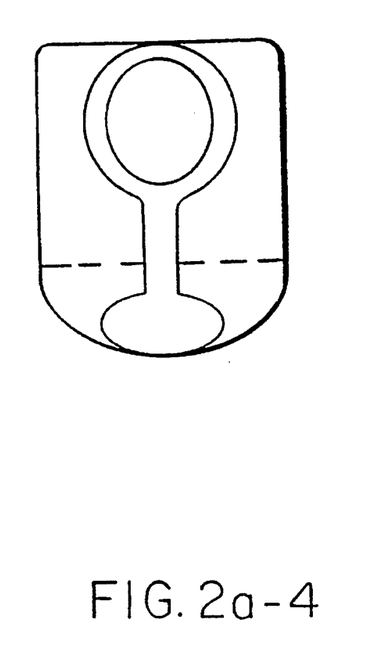
Figure 2B:
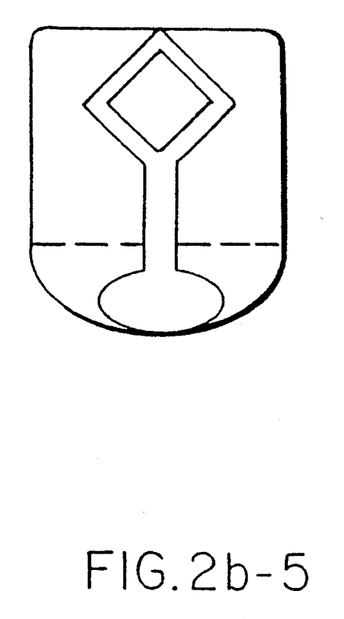
Figure 2B:
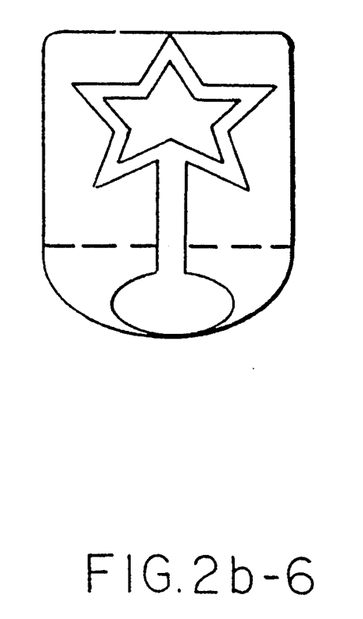
Figure 2B:
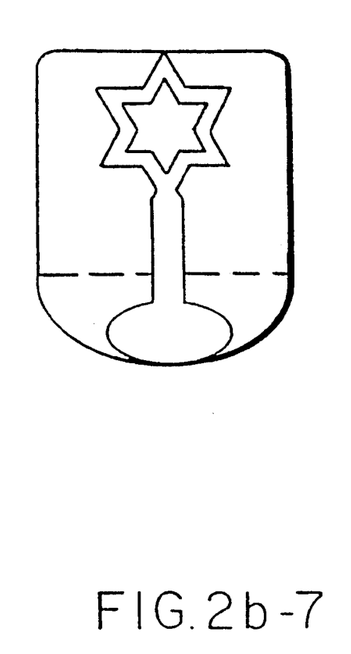
Figure 2B:
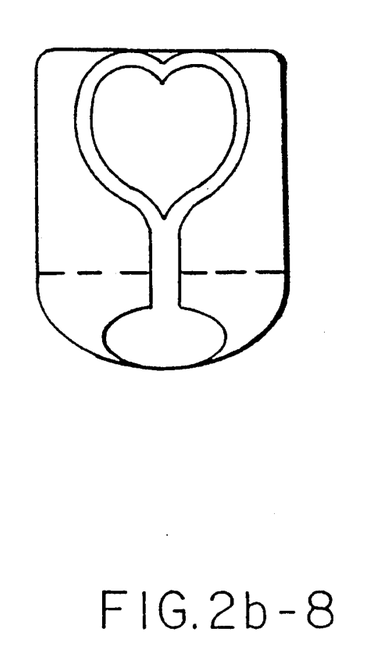
Figure 2C:
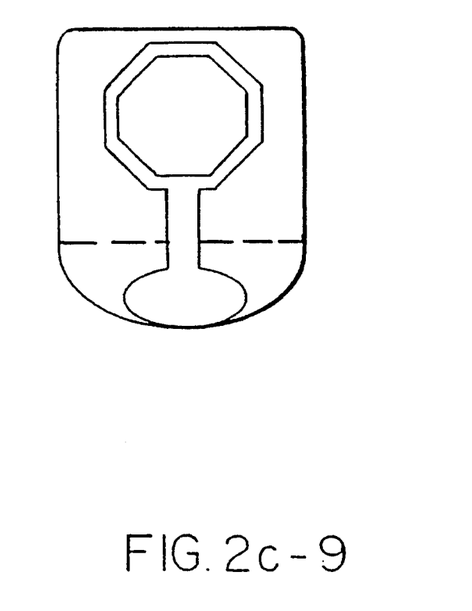
Figure 2C:
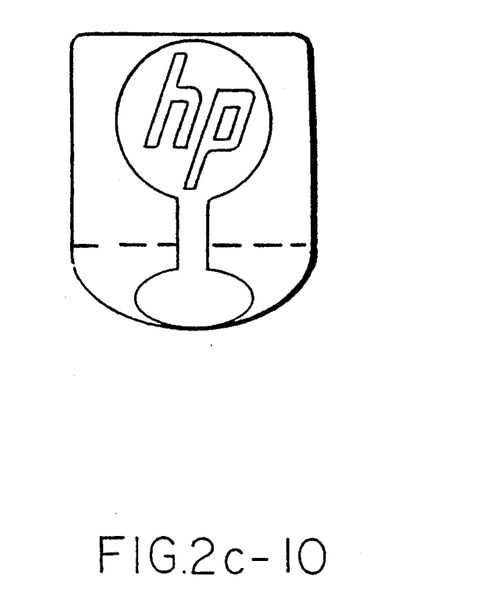
Figure 2C:
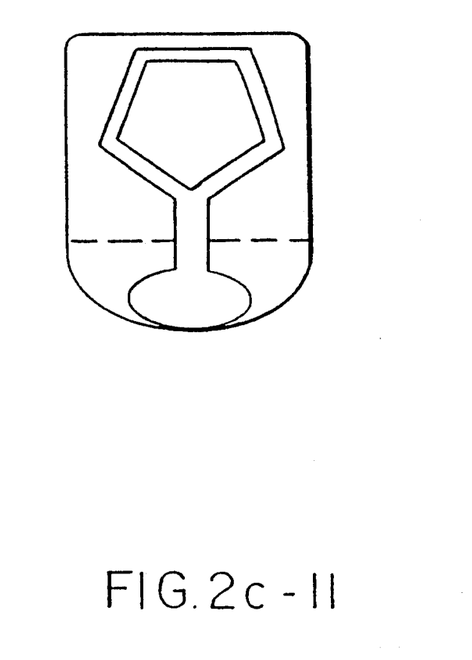
Figure 2C:
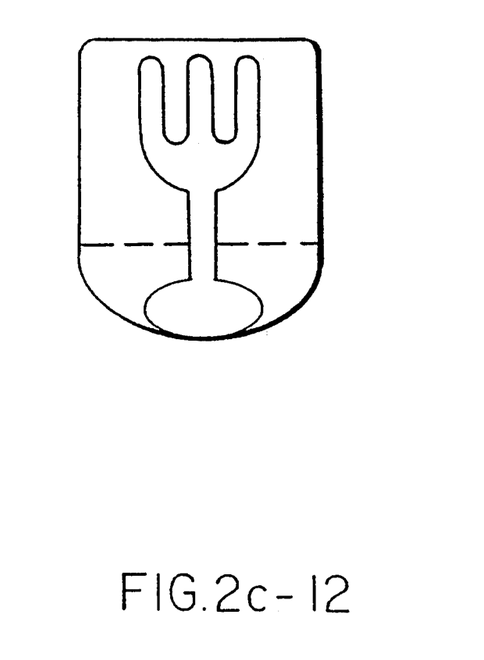

The components of one preferred biomedical electrode of the present invention are shown in FIG. 1. The non-conductive backing material 1 contains a first surface and a second surface. The first surface is divided into two areas 2 and 3, and may be used for printing specific decorations and/or instructions in register on each specific electrode. A typical placement site for instructions 4 for an EKG electrode is illustrated as "Vi". The second surface of the non-conductive backing material 1 also has two areas 5 and 6, corresponding to the first surface areas 2 and 3. Both areas 5 and 6 are at least partially covered with a printed design of conductive ink 7 and 8. The printed design of conductive ink is considered to have two components, pattern 7 and shaft 8. Pattern 7 is smaller than area 5 and is generally centered on area 5 of the non-conductive backing material 1. Shaft 8 is smaller than area 6 and is generally centered on area 6 of non-conductive backing material 1. Taken together, areas 3 and 6 of non-conductive backing material 1, along with shaft 8, form tab 9, the purpose of which is to accept an electrical connector (not shown).

The conductive-adhesive electrolyte layer 10 has two surfaces, upper surface 11 and lower surface 12. The upper surface 11 of conductive-adhesive electrolyte layer 10 covers pattern 7 of the conductive ink as well as area 5 of backing material 1, while leaving shaft 8 of the conductive ink and area 6 of non-conductive backing material 1 exposed. Shaft 8 and area 6 will remain free from the skin when the electrode is applied and serve as a means of connecting a leadwire clip to the electrode. In another embodiment (not shown), the electrode can be manufactured with a snap stud secured to the tab, permitting the traditional leadwire socket-to-snap connection.

Lower surface 12 of conductive-adhesive electrolyte layer 10 is covered by upper surface 14 of protective release liner 13. Upper surface 14 of the release liner 13 generally has a silicone coating 15 which allows the release of conductive-adhesive layer 10 from release liner 13 without delaminating conductive-adhesive layer 10 from area 5 of backing material 1. Such release liners are well known to those practiced in the art. Lower surface 16 of the release liner 13 may be coated or not coated, and may be printed or not printed, as desired. A phantom outline 17 of backing material 1 is produced upon the upper surface 14 of release liner 13 in the process of die cutting.

In using the electrode or set of electrodes in accordance with the present invention, the user first identifies the specific body site on which each specific electrode must be placed. This identification is made through either reading the instruction printed on the back of the non-conductive backing material or by identifying the specific electrode by its size and/or shape. Second, the release liner 13 is removed from the selected electrode. The now exposed conductive-adhesive face 12 is then pressed onto the selected body site. A leadwire clip is attached to the exposed tab (shaft 6 and surface 8) which is free of conductive-adhesive material. (Alternatively, the electrode's tab can be fitted with a snap connector in order to accept a snap-socket leadwire). Said lead wire is connected to an instrument which monitors electrode signals. When electric impulses are generated from the body, their signals are transmitted sequentially through the skin to the electrode to the leadwire and finally to the monitoring instrument.

The non-conductive backing material is generally made of polyester material and, for a single typical electrode, has a surface area of from about 0.75 square inches ("in$^2$") to about 1.50 in$^2$, preferably from about 0.85 in$^2$ to about 1.25 in$^2$, and most preferably from about 0.95 in$^2$ to about 1.15 in$^2$. One especially preferred polyester material is 2 mil ICI 329 Melinex film, (ICI Films, Inc., Wilmington, Del.).

The inks which can be employed in accordance with the present invention include either 1) an ink comprising a galvanic metal, such as silver, and a conductive salt, such as silver chloride, such that the galvanic metal to conductive salt ratio (by weight) is between about 7:3 and about 9:1, or 2) a homogeneous blend of inks including a first ink comprising a galvanic metal, such as silver, and a conductive salt, such as silver chloride, such that the galvanic metal to conductive salt ratio (by weight) is between about 7:3 and about 9:1, and a second ink comprising an inert, carbon based material, such as carbon. In general, the weight percent of ink components used in accordance with the present invention comprise 0% to 90% carbon, 10% to 100% silver, and 5% to 20% silver chloride.

In addition to silver, the galvanic metal may be tin, gold, or platinum. The conductive salts to be used in conjunction with silver, tin, gold and platinum, respectively, are silver chloride, tin chloride, gold chloride and platinum chloride. In addition to carbon, the inert, carbon based material may be graphite.

The conductive salt is ordinarily present in biomedical electrodes because it resists polarization, enabling the product to meet the AAMI standards for Defibrillation Overload Recovery. By policy, most medical facilities require that all electrodes meet this standard.

Preferred inks which can be used in accordance with the present invention include CMI-108-38 ink (whose conductive components are 100% silver and silver chloride and which has a silver/silver chloride ratio of 9:1), CMI-107-23 ink (whose conductive components are 100% carbon based), Olin Hunt ink 7019 (whose conductive components are 100% silver and silver chloride and which has a silver/silver chloride ratio of 9:1), and Olin Hunt ink 440A (whose conductive components are 100% carbon based). The CMI inks are manufactured by Creative Materials, Inc., in Tyngsboro, Mass. The Olin Hunt inks are manufactured by Olin Hunt, Inc. in Ontario, Calif.

As noted above, the ink or homogeneous blend of inks can be printed onto the non-conductive backing material in a predetermined design consisting of a predetermined pattern and a shaft for electrical connection to a leadwire. When the conductive ink is so printed, in such a pattern, it partially covers the non-conductive backing material and the conductive adhesive layer, since the area of the conductive ink layer designated in FIG. 1 as "pattern 7" (hereinafter, "the pattern") covers only a portion of the adhesive layer and only a portion of the area of the non-conductive backing material designated in FIG. 1 as "area 5" (hereinafter, "the backing face"). Preferably, the predetermined design must be electrically continuous, and special care must be taken to adequately coat the tab portion where the electrical connection to the monitor is made. The pattern as a percentage relative to the surface area of the conductive adhesive layer (hereinafter, the "ink surface coverage") will, in part, be dictated by the desired impedance of the electrode and may completely cover the conductive adhesive layer, but generally it is between about 7% and about 90%, preferably between about 14% and about 28%. FIG. 2 illustrates a number of such patterns in which the ink surface coverage is between 15% and 40% when the conductive adhesive layer contacts all of the backing face not contacting the pattern.

The relative weight percent of components which can be used in the conductive ink layer of an electrode having a predetermined impedance is determined, in part, by the ink surface coverage of that electrode. For example, when the ink surface coverage is in the range of about 7% to 90%, it is preferred to use a homogeneous ink blend in which the silver plus silver chloride components are about 20%–90% by weight and the carbon component is about 80%–10% by weight. When the ink surface coverage is in the preferred range of about 14% to 28%, it is preferred to use a homogeneous ink blend in which the silver plus silver chloride components are about 70%–90% by weight and the carbon component is about 10%–30% by weight. For purposes of clarity, a blend in which the silver components (i.e., silver plus silver chloride) are 70% by weight and the carbon component is 30% by weight will be referred to as a blend with a silver/silver chloride to carbon ratio of 70/30.

The thickness of the conductive ink layer of the present invention is generally in the range of 0.1 to 0.8 mils, preferably in the range of 0.2 to 0.6 mils, and most preferably in the range of 0.3 to 0.5 mils.

The adhesive layer of the present invention can be either a UV curable adhesive, a hot melt adhesive or a combination thereof. When the adhesive is of the UV curable type, the adhesive is preferably cured before attaching the protective release liner. UV curable adhesives are well known in the art. Preferred UV curable adhesives include Ludlow No. 1504-G10 and Ludlow No. 1601, both of which are experimental adhesives obtained from Findley Adhesives Inc., Wauwatosa, Wis. under the designations M 3095 and M 3096, respectively.

As noted above, hot melt adhesives may also be used in accordance with the present invention. The advantages gained from using a hot melt adhesive are that 1) fewer process steps are required, and 2) the tack level of the conductive-adhesive is easily controlled by varying the thickness of the coating. Preferred hot melt adhesives have application temperatures of less than about 200° F. and are water based, and so avoid problems associated with the use of solvent based adhesives. Water-based, polymeric, hot-melt adhesives are derived from an essentially solventless process and can be coated directly onto the printed backing face in a single manufacturing process. Preferred water based hot melt adhesives include Ludlow Nos. 2179, 2254 and 2255. These three adhesives are experimental adhesives obtained from H. B. Fuller Co., St. Paul, Minn., under the designations 2179, 2254, and 2255, respectively.

The thickness of the conductive adhesive layer is generally in the range of 10 to 25 mils, preferably 14 to 20 mils, most preferably 16 to 18 mils.

The protective release liner is generally made of a silicone coated polyester film or a silicone coated paper substrate and, for a single typical electrode, has a surface area adequate to protect the entire surface of the electrode or set of electrodes. One especially preferred release liner is the 5 mil polyester film, silicone coated on each side, manufactured by Daubert Coated Products in Dixon, Ill.

In one preferred embodiment of the present invention (hereinafter, "embodiment A"), there is provided an electrode for detecting biological signals in mammals which comprises: a) a non-conductive backing material having a first side for graphics which optionally includes labelling the electrode for its intended placement, and a second side contacted by a conductive ink layer; b) a conductive adhesive layer contacting the conductive ink layer; and c) a protective release liner which contacts the conductive adhesive layer, wherein the conductive adhesive layer is between the layer of conductive ink and the protective release liner. In this embodiment, the conductive ink layer comprises a homogeneous blend of inks including a first ink comprising silver and silver salt and a second ink comprising at least one other inert, carbon-based conductive material, such as carbon or graphite. The adhesive layer of such an electrode may be (i) a hot melt adhesive, (ii) a UV curable adhesive or (iii) an adhesive comprising a hot melt adhesive component and a UV curable adhesive component.

In another preferred embodiment of the present invention (hereinafter, "embodiment B"), there is provided an electrode which is substantially similar to embodiment A, except that a) the second side of the non-conductive backing layer is partially covered by a conductive ink layer; and b) the conductive adhesive layer covers both the conductive ink layer and the non-conductive backing material not in contact with said conductive ink layer. The contact between the adhesive layer and the pattern of conductive ink in such an electrode enables the use of an electrode having a predetermined ink surface coverage and/or a predetermined pattern of conductive ink. The predetermined pattern may be any number of patterns, including those illustrated in FIGS. 2 and 4, namely an octagon, a pentagon, arbitrary lettering, a trident, a diamond, a five pointed star, a heart, a six pointed star, a circle, an oval, a cross hatched circle, or a hollow circle of uneven width.

In accordance with another aspect of the present invention, there is provided a kit or set of electrodes wherein each electrode is designed to produce a particular impedance value especially suited for its intended placement at a particular body site. This aspect of the invention permits the differentiation of biomedical electrodes within a set of electrodes designed for a particular monitoring procedure, e.g. ECG/EKG monitoring or stress testing- Selective placement of impedance distinct electrodes can help to compensate for these different body site impedances and greatly improve the accuracy of the readings. As noted above, the human body exhibits different skin impedance values at various sites. For example, it is not unusual for impedances in diverse body sites to differ by as much as 150%. Traditionally, skin impedance is equalized by means of skin preparation, which consists of abrading away the surface layer with a coarse material such as Scotchbrite$^R$, sandpaper, or steel wool; or by utilizing an abrasive electric burr or drill. However, owing to time limitations, many procedures, especially resting electrocardiograms, are performed without the benefit of skin preparation to equalize impedance. Therefore, it may be desirable to compensate for these differences in impedance at the electrode/skin interface at various body sites and utilize electrodes which have inherent impedance values tailored to the body site on which they are placed. For example, it would be useful for health care specialists such as cardiologists to be provided with a set of EKG electrodes wherein the impedances the electrodes compensate for the variance in skin impedance at different body sites. Also, different brands/models of monitors do not necessarily produce consistent results from the same electrode. Thus, the impedances of the electrodes must often be geared to a specific monitor in order to produce the best tracing. The present invention also allows for use of impedance distinct electrodes which compensate for the different performances of individual brands and models of patient monitors. The electrodes of the present invention generally provide impedances which may range between 10 and 2000 ohms, preferably 50 and 1000 ohms, and most preferably 75 and 500 ohms, at 10 Hz. In other preferred embodiments of the present invention, the impedance of each electrode within a set may be the same.

The impedance of each electrode can be controlled by varying one or more of 1) the amount of conductive ink (i.e., either the ink surface coverage and/or the thickness of the ink layer), or 2) the blend of conductive inks. The impedance of any single electrode prepared in accordance with the present invention can be readily measured by use of standard equipment such as the Xtra Tech ECG Electrode Tester, Model No. ET-65A, manufactured by Direct Design Corp., Lenexa, Kans.

Figure 3:
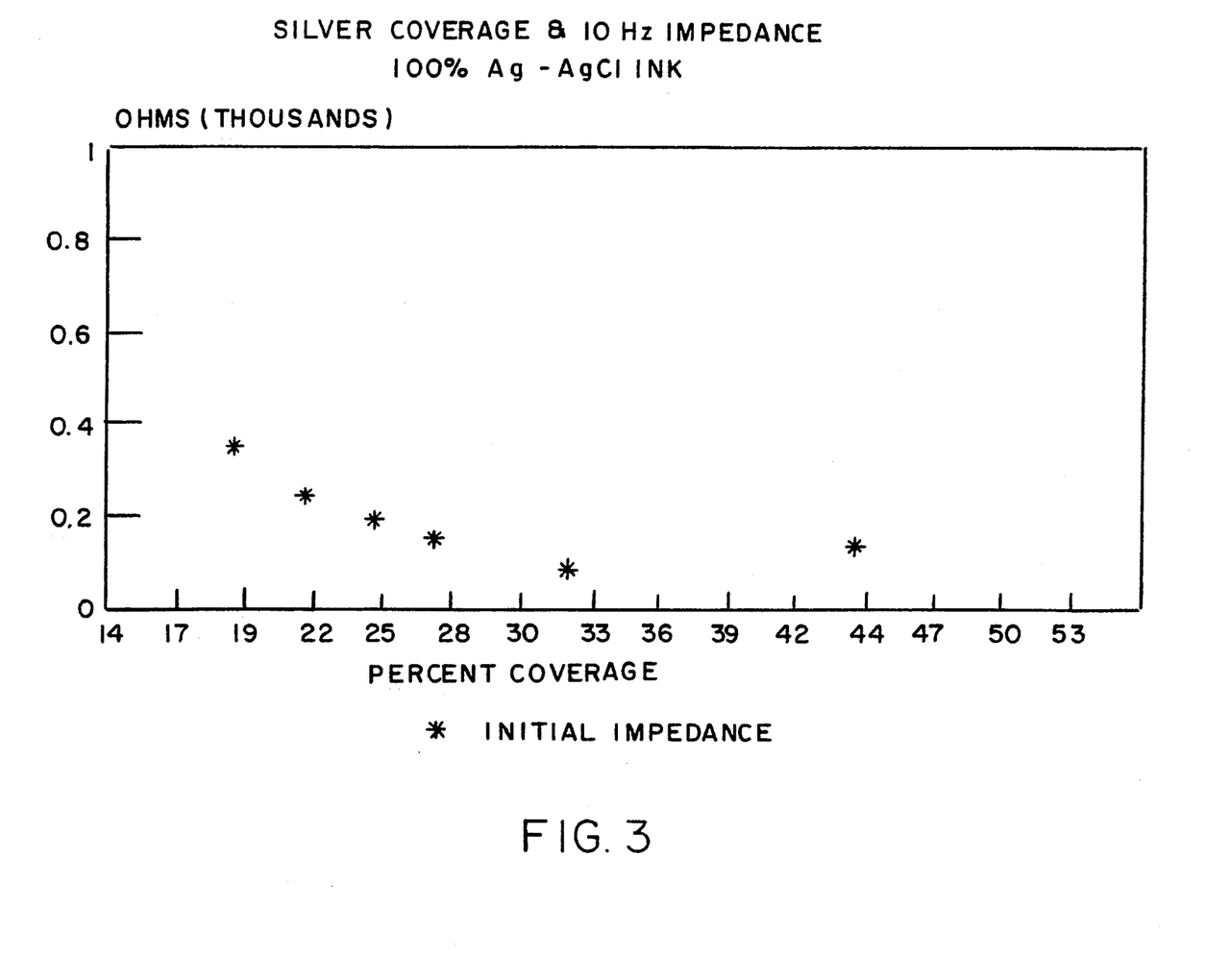
FIG. 3 is a chart demonstrating how impedance varies as a function of ink surface coverage.

The preferred means for making an electrode having a predetermined impedance is by varying the ink surface coverage of the electrode. In general, increasing the ink surface coverage decreases the impedance of the electrode. For example, FIG. 3 illustrates the impedances of electrodes of various ink surface coverages, ranging from about 14% to about 56%. The ink used in each of these electrodes is CMI-108-38, wherein the conductive components in the ink are 100% silver and silver chloride (90% silver and 10% silver chloride). The thickness of the ink layer is 10 microns. The non-conductive backing layer has a total surface area on one side of 1.1281 in$^2$ wherein the backing face has an area of 0.81 in$^2$. The adhesive is Ludlow GEL Formula 2179 and has a thickness of about 16 mils, and covers ("coincides with") at least the predetermined pattern and the backing face. As can be seen from FIG. 3, when the pattern printed on the backing face is about 0.16 in$^2$ (thus providing an ink surface coverage of about 19.8%), the initial impedance at 10 Hz is about 350 ohms. When everything but the pattern is held constant and the pattern is changed to about 0.206 in$^2$ (thus providing an ink surface coverage of about 25.4%), the initial impedance at 10 Hz is less than about 200 ohms. Although not shown, increasing the ink surface coverage past about 50% results in impedances in the range of 50–100 ohms at 10 hz. Also, although not shown, decreasing the ink surface coverage below 14% continues to increase the impedance exponentially. For example, when the ink surface coverage of an electrode whose conditions are similar to those in FIG. 3 is reduced to less than about 8 percent, the resulting impedance is about 2000 ohms at 10 hz.

Figure 4:
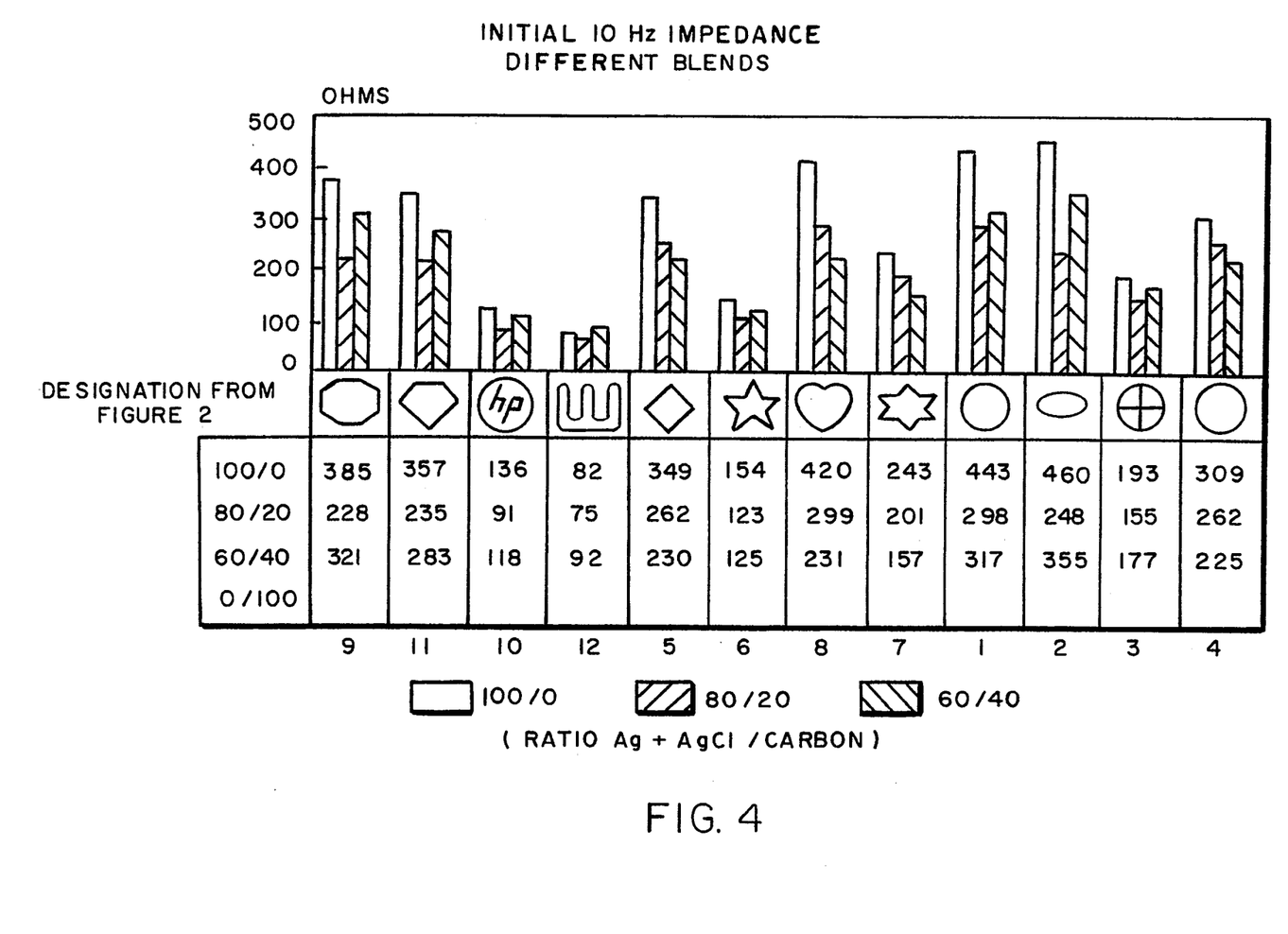
FIG. 4 is a chart demonstrating how impedance varies with ink blend.

The blend of inks can also be used to vary the impedance of each electrode in a set or kit of electrodes. As noted above, the electrodes of the present invention may have silver/silver chloride to carbon ratios between about 10/90 and about 100/0, although for the preferred ink surface coverages described above these ratios are between about 70/30 and about 90/10. FIG. 4 illustrates the change in impedance in a number of electrodes having different patterns when the ink blend for each pattern was varied to have silver/silver chloride to carbon ratios of 100/0, 80/20 and 60/40. As can be seen from FIG. 4, varying the ink blend for any particular pattern results in changing the impedance of that electrode. Thus, the impedance of an electrode can be readily modified by changing the ink blend and ascertaining the impedance of a particular blend by the use of the Xtra Tech ECG Electrode Tester, described above.

Figure 5:
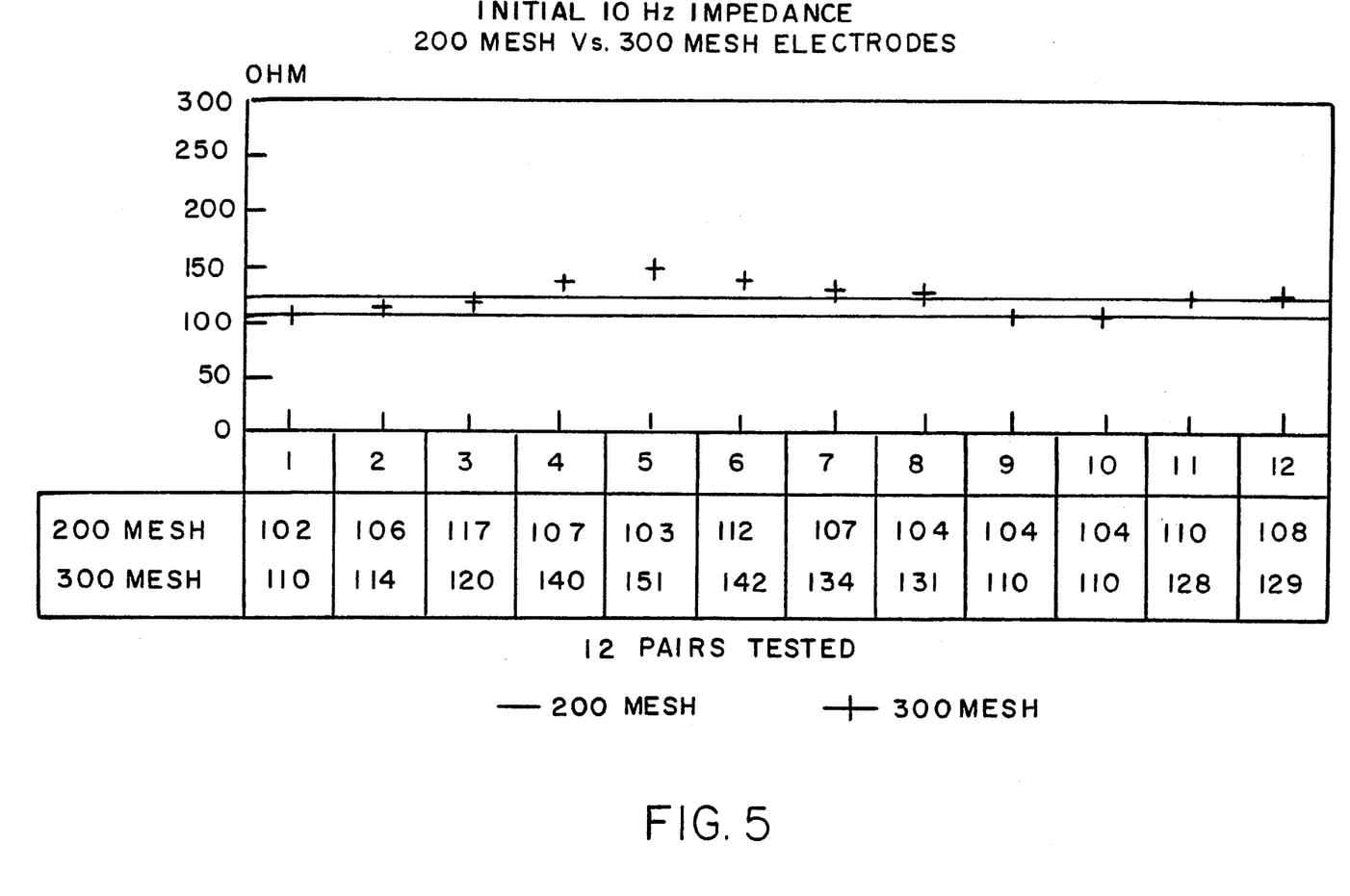
FIG. 5 is a chart demonstrating how impedance varies as a function of the thickness of the ink layer.

The impedance of electrodes within a set may also be controlled by varying the thickness of the conductive ink layer. FIG. 5 shows how impedance may be increased by decreasing the thickness of the ink layer in the electrode. Specifically, Pair No. 1 of FIG. 5 refers to two electrodes each of which comprises a non-conductive backing layer whose surface area is 1.1281 in.$^2$ and whose backing face area is 0.81 in$^2$, a pattern in the shape of a cross hatch having an area of about 0.16 in$^2$, a blend of Olin Hunt 7019 and 440A inks whose silver/silver chloride to carbon ratio is 80/20, and a Ludlow 1504-G10 GEL adhesive whose thickness is 18 mils and which coincides with the 0.81 in$^2$ backing face, thus producing an ink surface coverage of about 19.8%. The first electrode of Pair No. 1, which has a 0.4 mil layer printed by a 200 mesh screen, displays an initial impedance of 102 ohms. The second electrode of Pair No. 1, which has with a 0.3 mil ink layer printed by a 300 mesh screen, displays an initial impedance of 110 ohms at 10 hz.

Thus, the skilled artisan will appreciate that the impedance of any particular electrode can be changed by varying one or more of the parameters discussed above by the amount necessary to produce the desired impedance. The impedance of the electrode thus produced can readily be ascertained by use of the Xtra Tech ECG Electrode Tester, described above.

In addition to controlling impedance values, printing patterns of conductive ink having a predetermined ink surface coverage allows for tight, predictable, repeatable specifications. Such control of specification may be important to the clinical use of these products in patient monitoring. Pattern printing in register with each electrode also reduces cost since none of the applied ink is stripped away after die-cutting, when the waste matrix is removed.

Figure 6:
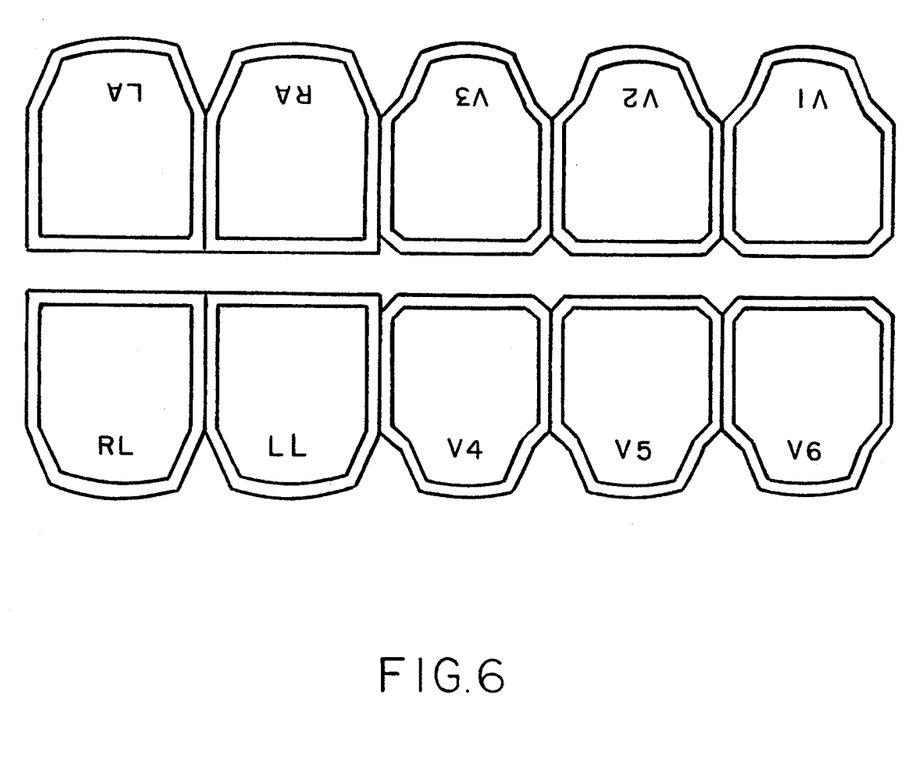
FIG. 6 is a top view of a set of a card containing a set of biomedical electrodes assembled onto a release liner, demonstrating the differentiation of biomedical electrodes within a set through different instructions.

A typical set of electrodes which carries instructions is shown in FIG. 6. These electrodes are designed for EKG use and carry instructions related to discrete body sites onto which they should be placed. For example, the electrodes described by the instructions as "V1" through "V6" must be placed at predetermined sites on the chest of the patient.

Figure 7:
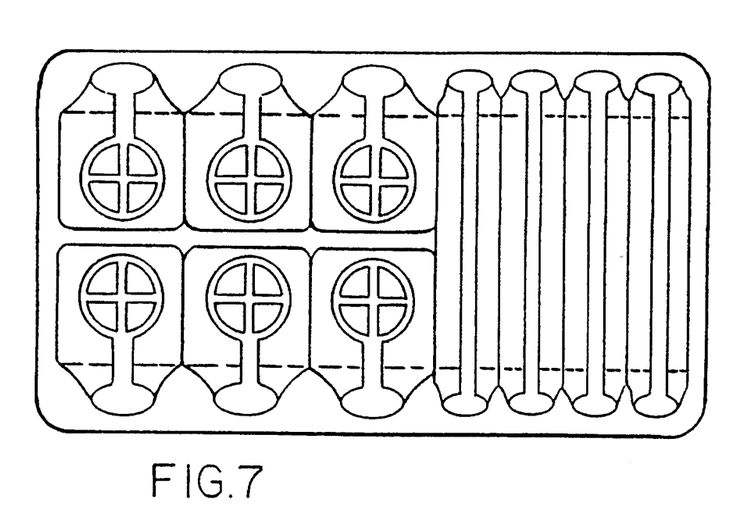
FIG. 7 is a top view showing a kit of electrodes of different sizes and shapes.

As further means of differentiating the appearance of electrodes possessing diverse impedances, the size and shade of the electrode may be varied within the set. For example, FIG. 7 shows electrodes of varying shapes and sizes. The different appearances assist the user in identifying and/or placing a given electrode in the correct site on the body. For example, the electrodes shown in FIG. 7 may be directed to EKG testing, wherein the long, thin electrodes are placed on the patient's wrists and ankles and the circular electrodes are placed on the patient's chest.

In another preferred embodiment of the present invention, (hereinafter,"embodiment C"), there is provided a kit for detecting biological signals in mammals comprising a plurality of electrodes, wherein each electrode may comprise the components of embodiments A or B, but wherein said plurality of electrodes comprises a first electrode having an impedance which differs from the remaining plurality of electrodes by at least about 15%, and preferably between 20% and 80%. The conductive ink layer of the electrodes in the set may be either a) an ink comprising silver and silver salt, or b) a blend of inks including a first ink comprising silver and silver salt and a second ink comprising an inert carbon based material. The first electrode may have an impedance value in the range of from about 10 to about 2000 ohms, preferably in the range of from about 50 to about 1000 ohms, and more preferably in the range of from about 75 to about 500 ohms, at 10 Hz. The impedance of the first electrode in such a kit may be provided by a) a predetermined amount of conductive ink (i.e., a predetermined degree of ink surface coverage or a predetermined thickness of the conductive ink layer) or b) a predetermined composition of the conductive ink layer.

The size and shape of at least one electrode in such a kit may also differ from the size and shape of another electrode in the kit to aid in the placement of the electrodes on particular body sites.

Coating the inks onto the nonconductive backing material may be accomplished via any number of known techniques such as screen printing, flexographic printing or rotogravure printing techniques. Screen printing is the preferred method of coating the inks onto the non-conductive backing material. In screen printing, a stencil representing the nonprinting areas is applied to a silk, nylon or stainless steel fine-mesh screen to which ink is applied and transferred to the surface to be printed by scraping with a rubber squeegee. In the flexographic printing technique, the ink is applied to a rubber or other elastomeric raised surface, which is brought into direct contact with the surface to be printed on. Lastly, in rotogravure printing, the nonprinting area is at a common surface level and the printing area is recessed and consists of wells etched or engraved, usually to different depths, inks are transferred to the whole surface and a metal blade is used to remove the excess ink from the non-printing surface.

The present invention also comprises a unique, continuous high speed method of manufacturing the invention utilizing one pass on a single production line. A preferred embodiment of that method is shown in FIG. 8.

Figure 8:
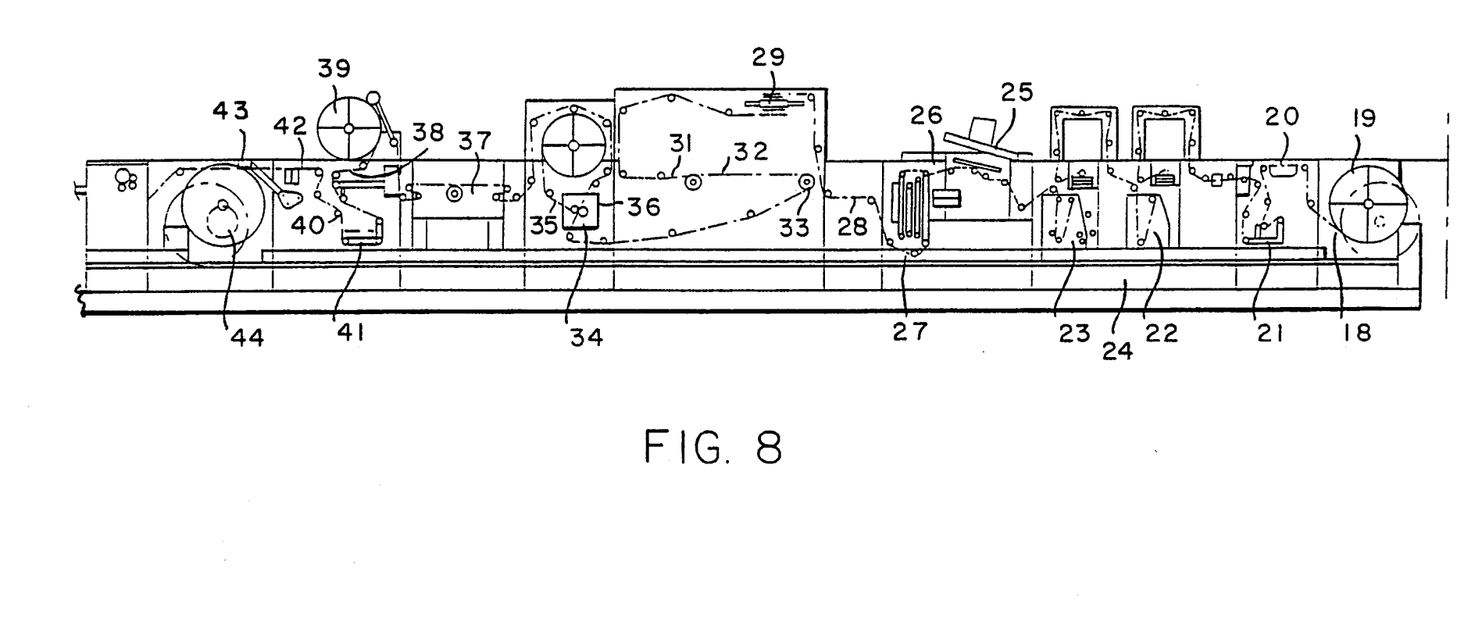
FIG. 8 is a schematic representation of a preferred continuous process for manufacturing biomedical electrodes of this invention.

Referring now to FIG. 8, a continuous web 18 of nonconductive backing material is fed from roll 19 through web cleaning station 20 and web alignment guide 21. The web of nonconductive backing material 18 then passes through a first flexographic printing station 22 and a second flexographic printing station 23 where two colors of ink are applied to the first surface 24 of the nonconductive backing material 18. The web then passes into a screen printing station 25 where a homogeneous blend of conductive ink is applied to the second surface 26 of the nonconductive backing material 18 in either a predetermined design or with full coverage. After the ink is applied, the printed web passes through drying station 27 where the ink is cured to a dry state, and is inspected for consistency and continuity at inspection station 28.

The web of nonconductive backing material 18 which has now been printed on both surfaces 24 and 26 passes through turnaround rollers 29 so that the second surface 26 is presented under the coating head 30 where a viscous conductive adhesive material 31 is applied so as to cover the pattern of conductive ink which has already been printed onto surface 26.

As noted, the conductive adhesive material 31 may be in the form of a hot melt adhesive, or a UV curable adhesive, or art adhesive comprising a hot melt adhesive and a UV curable component. If there is a requirement for UV curing, the web passes immediately from the coating head 30 into an ultraviolet oven 32, and therefrom over a chill roller 33 which cools the coated web.

The web 18 which has now been printed on both surfaces 24 and 26 and also coated with conductive adhesive material 31 passes into a laminating station 34 where a protective release liner 35 is applied over the conductive adhesive material 31.

At this point in the process the construction of the product is complete and the composite 36 passes into a first die cutting station 37 where it is cut into individual electrodes of predetermined sizes and shapes. Upon departing the first die cutting station 37 the web of waste material 38 is removed from in between the individual electrodes which have been cut from composite 36. The web of waste material 38 is wound up on roller 39.

At this point the construction consists of individual electrodes on a continuous web 40 of protective release liner 35. The construction 40 passes through a web alignment guide 41 and then into a second die cutting station 42 where the protective release liner 35 is cut into predetermined shapes to form a kit of electrodes all contained on a single sheet of said release liner 35. A web of waste release liner 43 which has been removed from in between the die cut sheets is wound onto roller 44.

The process is now complete and the resulting product is a sheet of protective release liner containing a kit of electrodes. This product is delivered from the second die cutting station 42 onto a takeaway belt 45 and subsequently removed to a packaging area.

In one preferred embodiment of the continuous process of the present invention, (hereinafter, "embodiment D"), there is provided a continuous process for manufacturing a biomedical electrode comprising, sequentially: (a) printing a conductive ink layer onto one side of a non-conductive backing material to form an inked substrate; (b) applying a conductive adhesive layer to the inked substrate so that the conductive ink layer contacts the conductive adhesive layer, and (c) attaching a protective release liner to the substrate, wherein the conductive ink layer and the adhesive layer are substantially similar to those disclosed in embodiments A, B or C. The method of printing the conductive ink layer in an electrode made from such a process may be either screen printing, flexographic printing or rotogravure printing, although screen printing is preferred. The curing of the conductive adhesive layer in an electrode made from such a process is preferably accomplished before attaching the protective release liner.

In another preferred embodiment of the present invention, (hereinafter "embodiment E"), there is provided a continuous process comprising steps which are substantially similar to those in embodiment D, except that the conductive ink layer partially covers the nonconductive backing material and the conductive adhesive layer. The partial coverage of the conductive ink may be due to a predetermined ink surface coverage or a predetermined pattern as disclosed in embodiment B.

In yet another preferred embodiment of the present invention, (hereinafter, "embodiment F"), there is provided a continuous process comprising steps substantially similar to embodiment D, except that embodiment F additionally requires die cutting the substrate to form a plurality of die cut portions having a predetermined shape and a waste material and stripping away the waste material from the die cut portions. The instructions on the remaining side of the non-conductive backing material typically contain printed graphics which optionally includes instructions. The shape or size of one electrode in a kit made from such a continuous process may differ in shape or size from at least one of the remaining plurality of electrodes in the kit.

In another preferred embodiment of the present invention (hereinafter, "embodiment G"), there is provided a continuous process substantially similar to embodiment F, except that the conductive ink layer partially covers the first side of a non-conductive backing material to form a patterned, inked substrate and partially covers the conductive adhesive layer. The remaining side of the non-conductive backing material contains graphics which optionally includes printed instructions. The predetermined patterns used in this embodiment may be identical to those disclosed in embodiment E.

Examples of some of the preferred embodiments of the present invention are discussed below. These examples are not intended in any way to be limitations upon the scope of the present invention.

EXAMPLES

Example 1

Electrode Comprising A Pattern in the Shape of A Cross Hatch With A Silver/Silver Chloride To Carbon Ratio Of 80/20

Figure 9:
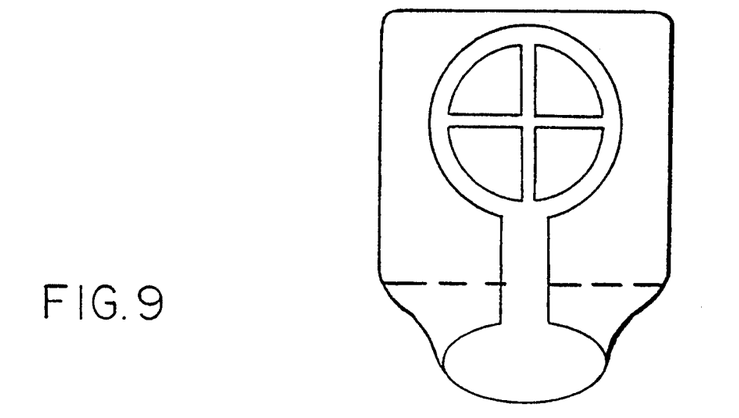
FIG. 9 displays the electrode and the dimensions thereof made through the process described in FIG. 8.

An electrode which displayed an impedance of 155 ohms at 10 hz when determined by AAMI standard test procedures was made as follows:

A continuous web 18 of nonconductive backing material made of polyester film with a width of 13 inches was fed from roll 19 through web cleaning station 20 and web alignment guide 21. The web of nonconductive backing material 18 then passed through a first flexographic printing station 22 and a second flexographic printing station 23 where two colors of ink (in this case, grey and blue were applied to the first surface 24 of the nonconductive backing material 18 so that the symbols "Ludlow" and "Sensatrace" appeared on the first surface of the nonconductive backing material. The web then passed into a screen printing station 25 where a homogeneous blend of conductive inks CMI-108-38 and CMI-107-23 whose silver/silver chloride to carbon ratio is 80/20 was applied to the second surface 26 of the nonconductive backing material 18 in a plurality of cross hatch patterns, each of which is displayed in FIG. 9. The pattern had an area of about 0.16 in$^2$ while the area designated by FIG. 1 as shaft 8 was about 0.11 in$^2$. The thickness of the ink layer was 0.4 mils. After the homogeneous blend of conductive ink was applied, the printed web passed through drying station 27 where the ink was cured at a temperature of 250° for six seconds to a dry state, and was inspected for consistency and continuity at inspection station 28.

The web of nonconductive backing material 18 which had been printed on both surfaces 24 and 26 passed through turnaround rollers 29 so that the second surface 26 was presented under the coating head 30 where a viscous conductive adhesive material 31, specifically Ludlow 1601, was applied at a thickness of 18 mils over a 0.81 in$^2$ area in a 0.9 inch×0.9 inch square. The adhesive covered at least all of the pattern which had already been printed onto surface 26. Because the area of the pattern was 0.16 in$^2$ and the area of the adhesive covering the pattern was 0.81 in$^2$, the ink surface coverage was about 19.8%.

The conductive adhesive material 31 was in the form of a UV curable adhesive. Because there was a requirement for UV curing, the web passed immediately from the coating head 30 into an ultraviolet oven 32 having a wavelength spectrum of between 200–400 nanometers for 6–9 seconds, and therefrom over a chill roller 33 whose temperature was 40° F. for 2–3 seconds.

The web 18, printed on both surfaces 24 and 26 and also coated with conductive adhesive material 31, passed into a laminating station 34 where a protective release liner 35, which was made of 5 mil silicone coated polyester and whose width was 12 inches, was applied over the conductive adhesive material At this point, the composite 36 passed into a first die cutting station 37 where it was cut into individual electrodes, producing an electrode with a non-conductive backing layer of 1.0077 in$^2$ whose backing face was 0.81 in$^2$, wherein the backing face coincided with the adhesive layer. Upon departing the first die cutting station 37, the web of waste material 38 was removed from in between the individual electrodes which had been cut from composite 36. The web of waste material 38 was wound up on roller 39.

At this point the construction consisted of individual electrodes on a continuous web 40 of protective release liner 35. The construction 40 passed through a web alignment guide 41 and then into a second die cutting station 42 where the protective release liner 35 was cut into a rectangular shape to form a kit of identical electrodes all contained on a single sheet of said release liner 35. A web of waste release liner 43 which had been removed from in between the die cut sheets was wound onto roller 44.

At this point the process was complete and the resulting product was a sheet of protective release liner containing a kit of identical electrodes. This product was delivered from the second die cutting station 42 onto a takeaway belt 45 and subsequently removed to a packaging area.

The electrode type made in the above process displayed an impedance of 155 ohms at 10 hz when determined the Xtra Tech ECG Electrode tester.

Example 2

Electrode Comprising A Pattern in the Shape of A Cross Hatch With Silver/Silver Chloride To Carbon Ratio of 60/40

An electrode displaying an impedance of 177 ohms at 10 hz was made substantially as described in Example 1, except that the blend of CMI-108-38 and CMI-107-23 conductive inks had a silver/silver chloride to carbon ratio of 60/40.

Example 3

A Set of Electrodes Comprising A Pattern in the Shape of A Cross Hatch and A Pattern In The Shape Of A Star Each With A Silver/Silver Chloride To Carbon Ratio of 80/20

A kit of electrodes wherein at least one electrode in the kit displays an impedance of 155 ohms and at least one electrode in the kit displays an impedance of 123 ohms can be made substantially as described in Example 1, except that the mask used to print the cross hatch ink patterns in Example 1 is altered so that at least one of the shapes on the mask is in the form of a five pointed star whose pattern area is 0.1838 in$^2$, producing an ink surface coverage of 0.227.

Example 4

Electrode Comprising A Pattern in the Shape of A Cross Hatch With A Carbon to Silver/Silver Chloride Ratio of 80/20 0.3 Mil Ink Thickness An electrode displaying an impedance of about 170 ohms at 10 hz can be made substantially as described in Example 1, except that the thickness of the conductive ink is about 0.3 mils.

Example 5

Electrode Comprising A Pattern in the Shape of A Oval With A Silver/Silver Chloride To Carbon Ratio of 80/20

An electrode displaying an impedance of 248 ohms at 10 hz was made substantially as described in Example 1, except that that the mask used to print the cross hatch ink patterns in Example 1 was altered so that all the patterns on the mask were in the form of a oval whose pattern area was 0.1532 in$^2$, producing an ink surface coverage of 0.189.

Example 6

Electrode Comprising A Pattern in the Shape of A Oval With A Silver/Silver Chloride To Carbon Ratio of 60/40

An electrode displaying an impedance of 355 ohms at 10 hz was made substantially as described in Example 5, except that the conductive ink had a silver/silver chloride to carbon ratio of 60/40.

EXAMPLE 7

A Set of Electrodes Comprising A Pattern in the Shape of A Oval and A Pattern In The Shape Of A Star Each With A Silver/Silver Chloride To Carbon Ratio of 80/20

A kit of electrodes wherein at least one electrode in the kit displays an impedance of 248 ohms and at least one electrode in the kit displays an impedance of 123 ohms can be made substantially as described in Example 5, except that the mask used to print the oval ink patterns in Example 5 is altered so that at least one of the patterns on the mask is in the form of a five pointed star whose pattern area is 0.1838 in$^2$, producing an ink surface coverage of 0.227.

Example 8

Electrode Comprising A Pattern in the Shape of A Oval With A Silver/Silver Chloride To Carbon Ratio of 80/20 With 0.3 Mil Ink Thickness

An electrode displaying an impedance of about 275 ohms can be made substantially as described in Example 5, except that the thickness of the conductive ink is about 0.3 mils.

Example 9

A Set Of Electrodes Comprising Cross Hatch Patterns With A Silver/Silver Chloride To Carbon Ratio Of 80/20

Figure 10:
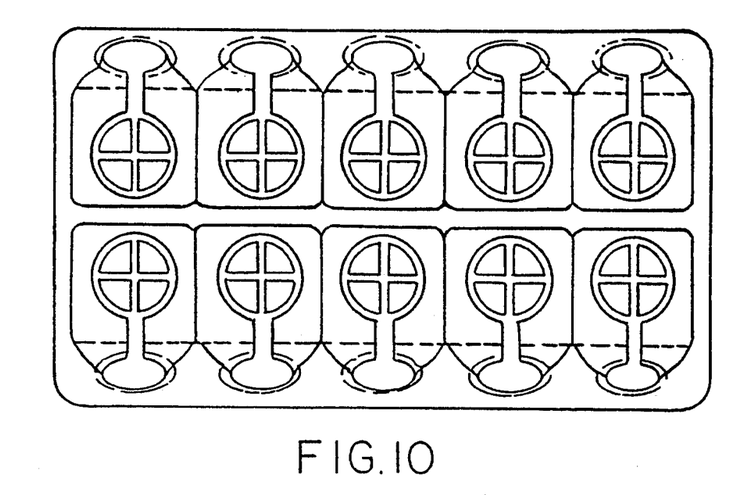
FIG. 10 is a top view of a preferred set of electrodes.

In one especially preferred embodiment, a set of EKG electrodes substantially similar to that shown in FIG. 10 is made as follows: The non-conductive backing layer of each electrode is made of a polyester film and has a surface area on one side of 1.1281 square inches, wherein the backing face is 0.81 in$^2$. The instructions on each electrode instruct the user to place that electrode on a specific part of the body. The ink is a blend of Olin Hunt inks 7019 and 440A, wherein the silver/silver chloride to carbon ratio is 80/20. The blend of ink is 72% silver, 8% silver chloride, and 20% carbon. The pattern portion of the conductive ink layer is a cross hatch, similar to that shown in FIG. 8, wherein the area of the pattern is about 0.16 in$^2$ while the area of the ink designated in FIG. 1 as the "shaft 8" is about 0.11 in$^2$. The thickness of the ink layer in the electrodes is about 0.5 mils. The adhesive used is a hot melt adhesive. The thickness of the adhesive layer is 18 mils. The adhesive is applied to coincide with the backing face over a 0.81 in$^2$ area in a 0.9 inch $\times$ 0.9 inch square and covers all of the pattern. Thus, the ink surface coverage is about 20%. The protective release liner is made of silicone coated polyester. The impedance of the electrode possessing the crosshatch pattern is 150 ohms at 10 hz. The process of printing the ink pattern onto the non-conductive backing layer is screen printing.

We claim:

1. A continuous process for fabricating a kit containing a plurality of biomedical electrodes, the impedances of the electrodes within the kit being variable in that at least one electrode in the kit has an impedance value that differs from an impedance value of at least one of the other electrodes within the kit, the electrodes being adaptable to be placed on the human skin at various predetermined locations for monitoring the electrical activity associated with physiological functioning of the heart that is manifested on the skin, the process being continuous from a starting point at which the electrodes exist in a disassembled state through an ending point at which complete functional electrodes are totally fabricated, all of the steps in the process being carried out on machinery in a predetermined sequence on a single pass through various stations in operation of the machinery, the process comprising the steps of:

a. providing a continuous web of a non electrically conductive backing material;
   b. advancing the web of backing material to a first station of the machinery;
   c. printing predetermined graphical information in register at a plurality of locations on a first side of the backing material, the printing being carried out at the first station of the machinery;
   d. advancing the web of backing material to a second station of the machinery;
   e. applying an electrically conductive ink in one or more predetermined patterns at a plurality of locations on a second side of the backing material, the ink being applied in register with the predetermined graphical information printed at the plurality of locations on the first side of the backing material, each predetermined pattern of conductive ink being selective to provide a desired impedance value for each electrode in the kit, the applying of the ink being carried out at the second station of the machinery;
   f. advancing the web of backing material to a third station of the machinery;
   g. applying an electrically conductive adhesive onto the conductive ink, the applying of the adhesive being carried out at the third station of the machinery;
   h. advancing the web of backing material to a fourth station of the machinery;
   i. applying a protective release liner over the electrically conductive adhesive, the applying of the protective release linear being carried out at the fourth station of the machinery;
   j. advancing the web of backing material to a fifth station of the machinery;
   k. die cutting the backing material to form a plurality of individual biomedical electrodes, each electrode comprising the backing material with the graphical information printed on one side, the conductive ink applied to the second side of the backing material, and the conductive adhesive applied onto the conductive ink, the die cutting of the backing material being carried out at the fifth station of the machinery;
   l. advancing the protective release liner to a sixth station of the machinery; and
   m. die cutting the release liner at a predetermined location to form a plurality of kits, each kit comprising a plurality of electrodes attached to a continuous portion of the die cut release liner, wherein the impedance value of at least one electrode within each kit differs from the impedance value of at least one of the other electrodes within that corresponding kit, the die cutting of the release liner being carried out at the sixth station of the machinery.

2. The continuous process of claim 1, wherein the step of printing graphical information at the plurality of locations on the first side of the backing material comprises the steps of:

a. flexographically printing predetermined graphical information of a first color in register at the plurality of locations on the first side of the backing material, the flexographic printing being carried out at the first station of the machinery;
   b. advancing the web of backing material beyond the first station of the machinery to a station intermediate the first and second stations of the machinery; and
   c. flexographically printing predetermined graphical information of a second color in register at the plurality of locations on the first side of the backing material, the flexographic printing of the information of the second color being carried out at the station intermediate the first and second stations.

3. The continuous process of claim 1, wherein the step of applying the conductive ink in one or more predetermined patterns at the plurality of locations on the second side of the backing material comprises the step of screen printing the conductive ink in one or more predetermined patterns at the plurality of locations on the second side of the backing material in register with the predetermined graphical information printed at the plurality of locations on the first side of the backing material.

4. The continuous process of claim 1, after the step of applying the conductive ink onto the second side of the backing material, further comprising the steps of:
   a. advancing the web of backing material beyond the second station of the machinery to a station intermediate the second and third stations of the machinery; and
   b. drying the ink, the step of drying the ink being carried out at the station intermediate the second and third stations.

5. The continuous process of claim 1, wherein the step of applying the protective release liner comprises the step of laminating the release liner to the conductive adhesive.

6. The continuous process of claim 1, wherein the step of applying a conductive ink in one or more predetermined patterns at the plurality of locations on a second side of the backing material comprises the step of applying the conductive ink in one or more predetermined patterns at the plurality of locations on a portion of the second side of the backing material in register with the predetermined graphical information printed at the plurality of locations on the first side of the backing material, the portion of the second side of the backing material covered by the conductive ink being predetermined by a desired impedance value of the conductive ink.

7. The continuous process of claim 1, wherein the step of applying the conductive ink in one or more predetermined patterns at the plurality of locations on the second side of the backing material comprises the step of flexographic printing the conductive ink in one or more predetermined patterns at the plurality of locations on the second side of the backing material in register with the predetermined graphical information printed at the plurality of locations on the first side of the backing material.

8. The continuous process of claim 1, wherein the step of applying the conductive ink in one or more predetermined patterns at the plurality of locations on the second side of the backing material comprises the step of rotogravure printing the conductive ink in one or more predetermined patterns at the plurality of locations on the second side of the backing material in register with the predetermined graphical information printed at the plurality of locations on the first side of the backing material.

9. The continuous process of claim 1, wherein the conductive ink comprises a homogenous mixture of silver and a silver salt.

10. The continuous process of claim 1, wherein the conductive ink comprises a homogeneous mixture of silver, a silver salt and at least one inert, carbon-based conductive material.

11. The continuous process of claim 1, wherein the electrically conductive adhesive comprises a hot melt adhesive.

12. The continuous process of claim 1, wherein the electrically conductive adhesive comprises a curable adhesive.

13. The continuous process of claim 12, after the step of applying the adhesive onto the conductive ink, further comprising the steps of:
   a. advancing the web of backing material beyond the third station of the machinery to a first intermediate station between the third and fourth stations; and
   b. curing the curable adhesive, the step of curing the curable adhesive being carried out at the first intermediate station.

14. The continuous process of claim 12, after the step of applying the adhesive onto the conductive ink, further comprising the steps of:
   a. advancing the web of backing material beyond the third station of the machinery to a first intermediate station between the third and fourth stations;
   b. curing the curable adhesive using ultraviolet energy, the step of curing the curable adhesive being carried out at the first intermediate station;
   c. advancing the web of backing material beyond the first intermediate station to a second intermediate station between the first intermediate station and the fourth station; and
   d. cooling the web of backing material, the step of cooling the web of backing material being carried out at the second intermediate station.

15. The continuous process of claim 1, wherein the conductive ink comprises a homogeneous mixture of a galvanic metal and a conductive salt.

16. The continuous process of claim 1, wherein the conductive ink comprises a homogeneous mixture of galvanic metal, a conductive salt, and at least one inert, carbon-based conductive material.

17. The continuous process of claim 1, wherein the nonelectrically conductive backing material comprises a polyester based material.

18. The continuous process of claim 1, wherein each predetermined pattern of conductive ink is selected to provide the desired impedance value for each electrode in the kit by selecting an amount of surface coverage of the ink on the second side of the backing material.

19. The continuous pattern of claim 1, wherein each predetermined pattern of conductive ink is selected to provide the desired impedance value for each electrode in the kit by selecting an overall thickness of the ink in the pattern.

20. The continuous process of claim 1, wherein each predetermined pattern of conductive ink is selected to provide the desired impedance value for each electrode in the kit by selecting a composition of materials comprising the ink.

* * * * *